United States Patent [19]

Mintz et al.

[11] Patent Number: 5,705,398
[45] Date of Patent: Jan. 6, 1998

[54] METHODS FOR IDENTIFYING INHIBITORS OF LPS-MEDIATED LBP BINDING

[75] Inventors: Douglas N. Mintz, New York, N.Y.; Peter Tobias, San Diego; Richard Ulevitch, Del Mar, both of Calif.

[73] Assignee: The Scripps Research Institute, La Jolla, Calif.

[21] Appl. No.: 205,719

[22] Filed: Mar. 2, 1994

[51] Int. Cl.$^6$ ................................. G01N 33/566
[52] U.S. Cl. ..................... 436/501; 435/7.1; 435/7.8
[58] Field of Search ....................... 435/7.32, 7.8, 435/975, 7.1; 530/300; 436/501

[56] References Cited

U.S. PATENT DOCUMENTS 4,207,075  6/1980  Liburdy.
5,543,303  8/1996  Goyert.

OTHER PUBLICATIONS

Mathison, et al., "Plasma Lipopolysaccharide (LPS)–Binding Protein, A Key Component in Macrophage Recognition of Gram–Negative LPS", *J. Immunol.*, 149: 200–206 (1992).
Wright, et al., "Lipopolysaccharide (LPS) Binding Protein Opsonizes LPS–Bearing Particles For Recognition By A Novel Receptor on Macrophages", *J. Exp. Med.*, 170: 1231–1241 (1989).
Wright, et al., "CD14, A Receptor for Complexes of Lipopolysaccharide (LPS) and LPS Binding Protein", *Science*, 249: 1431–1433 (1990).
Heumann, et al., "Control. of Lipopolysaccharide (LPS) Binding and LPS–Induced Tumor Necrosis Factor Secretion in Human Peripheral Blood Monocytes", *J. of Immunol.*, 148: 3505–3512 (1992).
Lee, et al., "Transfection of CD14 into 70Z/3 Cells Dramatically Enhances the Sensitivity to Complexes of Lipopolysaccharide (LPS) and LPS Binding Protein", *J. Exp. Med.*, 175: 1697–1705 (1992).
Tobias et al., Am. J. Respir Cell Mol. Biol. Supt. 1992 7(3):239–245.
Haziot et al, J. Immunol. 1993, 151(3):1500–1507.
Lynn et al, Immunology Today, 1992, 13(7):271–276.
Paurillo, NEIM, May 20, 1993, 328 (20):1471–1427.
Heumann et al, Journal of Immunological Methods, 1994, 171:169–176.
Hemmlla in Chemical Analysis v. 177 "Applications of fluorescence in Immunoassays", 1991 Wiley & Sons Inc. pp. 186–205.

*Primary Examiner*—Marianne P. Allen
*Assistant Examiner*—Patricia A. Duffy
*Attorney, Agent, or Firm*—Thomas Fitting; Emily Holmes

[57] ABSTRACT

The present invention describes a rapid method for the identification of compounds/reagents which inhibit lipopolysaccharide (LPS) binding to LPS binding protein (LBP), and kits for practicing the method.

12 Claims, 3 Drawing Sheets

5,705,398

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1128 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..1125

( x i ) SEQUENCE DESCRIPTION: SEQ ID NO:1:

```
ATG GAG CGC GCG TCC TGC TTG TTG CTG CTG CTG CTG CCG CTG GTG CAC        48
Met Glu Arg Ala Ser Cys Leu Leu Leu Leu Leu Leu Pro Leu Val His
 1               5                  10                  15

GTC TCT GCG ACC ACG CCA GAA CCT TGT GAG CTG GAC GAT GAA GAT TTC        96
Val Ser Ala Thr Thr Pro Glu Pro Cys Glu Leu Asp Asp Glu Asp Phe
             20                  25                  30

CGC TGC GTC TGC AAC TTC TCC GAA CCT CAG CCC GAC TGG TCC GAA GCC       144
Arg Cys Val Cys Asn Phe Ser Glu Pro Gln Pro Asp Trp Ser Glu Ala
         35                  40                  45

TTC CAG TGT GTG TCT GCA GTA GAG GTG GAG ATC CAT GCC GGC GGT CTC       192
Phe Gln Cys Val Ser Ala Val Glu Val Glu Ile His Ala Gly Gly Leu
     50                  55                  60

AAC CTA GAG CCG TTT CTA AAG CGC GTC GAT GCG GAC CGC GAC CCG CGG       240
Asn Leu Glu Pro Phe Leu Lys Arg Val Asp Ala Asp Arg Asp Pro Arg
 65                  70                  75                  80

CAG TAT GCT GAC ACG GTC AAG GCT CTC CGC GTG CGG CGG CTC ACA GTG       288
Gln Tyr Ala Asp Thr Val Lys Ala Leu Arg Val Arg Arg Leu Thr Val
                 85                  90                  95

GGA GCC GCA CAG GTT CCT GCT CAG CTA CTG GTA GGC GCC CTG CGT GTG       336
Gly Ala Ala Gln Val Pro Ala Gln Leu Leu Val Gly Ala Leu Arg Val
                100                 105                 110

CTA GCG TAC TCC CGC CTC AAG GAA CTG ACG CTC GAG GAC CTA AAG ATA       384
Leu Ala Tyr Ser Arg Leu Lys Glu Leu Thr Leu Glu Asp Leu Lys Ile
            115                 120                 125

ACC GGC ACC ATG CCT CCG CTG CCT CTG GAA GCC ACA GGA CTT GCA CTT       432
Thr Gly Thr Met Pro Pro Leu Pro Leu Glu Ala Thr Gly Leu Ala Leu
        130                 135                 140

TCC AGC TTG CGC CTA CGC AAC GTG TCG TGG GCG ACA GGG CGT TCT TGG       480
```

| | | | | | | | | | | | | | | | | |
|---|---|---|---|---|---|---|---|---|---|---|---|---|---|---|---|---|
| Ser<br>145 | Ser | Leu | Arg | Leu<br>150 | Arg | Asn | Val | Ser | Trp<br>155 | Ala | Thr | Gly | Arg | Ser | Trp<br>160 | |
| CTC | GCC | GAG | CTG | CAG | CAG | TGG | CTC | AAG | CCA | GGC | CTC | AAG | GTA | CTG | AGC | 528 |
| Leu | Ala | Glu | Leu | Gln<br>165 | Gln | Trp | Leu | Lys | Pro<br>170 | Gly | Leu | Lys | Val | Leu<br>175 | Ser | |
| ATT | GCC | CAA | GCA | CAC | TCG | CCT | GCC | TTT | TCC | TGC | GAA | CAG | GTT | CGC | GCC | 576 |
| Ile | Ala | Gln | Ala<br>180 | His | Ser | Pro | Ala | Phe<br>185 | Ser | Cys | Glu | Gln | Val<br>190 | Arg | Ala | |
| TTC | CCG | GCC | CTT | ACC | AGC | CTA | GAC | CTG | TCT | GAC | AAT | CCT | GGA | CTG | GGC | 624 |
| Phe | Pro | Ala<br>195 | Leu | Thr | Ser | Leu | Asp<br>200 | Leu | Ser | Asp | Asn | Pro<br>205 | Gly | Leu | Gly | |
| GAA | CGC | GGA | CTG | ATG | GCG | GCT | CTC | TGT | CCC | CAC | AAG | TTC | CCG | GCC | ATC | 672 |
| Glu | Arg<br>210 | Gly | Leu | Met | Ala | Ala<br>215 | Leu | Cys | Pro | His | Lys<br>220 | Phe | Pro | Ala | Ile | |
| CAG | AAT | CTA | GCG | CTG | CGC | AAC | ACA | GGA | ATG | GAG | ACG | CCC | ACA | GGC | GTG | 720 |
| Gln | Asn<br>225 | Leu | Ala | Leu | Arg<br>230 | Asn | Thr | Gly | Met | Glu<br>235 | Thr | Pro | Thr | Gly | Val<br>240 | |
| TGC | GCC | GCA | CTG | GCG | GCG | GCA | GGT | GTG | CAG | CCC | CAC | AGC | CTA | GAC | CTC | 768 |
| Cys | Ala | Ala | Leu | Ala<br>245 | Ala | Ala | Gly | Val | Gln<br>250 | Pro | His | Ser | Leu | Asp<br>255 | Leu | |
| AGC | CAC | AAC | TCG | CTG | CGC | GCC | ACC | GTA | AAC | CCT | AGC | GCT | CCG | AGA | TGC | 816 |
| Ser | His | Asn | Ser<br>260 | Leu | Arg | Ala | Thr | Val<br>265 | Asn | Pro | Ser | Ala | Pro<br>270 | Arg | Cys | |
| ATG | TGG | TCC | AGC | GCC | CTG | AAC | TCC | CTC | AAT | CTG | TCG | TTC | GCT | GGG | CTG | 864 |
| Met | Trp | Ser<br>275 | Ser | Ala | Leu | Asn | Ser<br>280 | Leu | Asn | Leu | Ser | Phe<br>285 | Ala | Gly | Leu | |
| GAA | CAG | GTG | CCT | AAA | GGA | CTG | CCA | GCC | AAG | CTC | AGA | GTG | CTC | GAT | CTC | 912 |
| Glu | Gln | Val<br>290 | Pro | Lys | Gly | Leu | Pro<br>295 | Ala | Lys | Leu | Arg | Val<br>300 | Leu | Asp | Leu | |
| AGC | TGC | AAC | AGA | CTG | AAC | AGG | GCG | CCG | CAG | CCT | GAC | GAG | CTG | CCC | GAG | 960 |
| Ser<br>305 | Cys | Asn | Arg | Leu | Asn<br>310 | Arg | Ala | Pro | Gln | Pro<br>315 | Asp | Glu | Leu | Pro | Glu<br>320 | |
| GTG | GAT | AAC | CTG | ACA | CTG | GAC | GGG | AAT | CCC | TTC | CTG | GTC | CCT | GGA | ACT | 1008 |
| Val | Asp | Asn | Leu | Thr<br>325 | Leu | Asp | Gly | Asn | Pro<br>330 | Phe | Leu | Val | Pro | Gly<br>335 | Thr | |
| GCC | CTC | CCC | CAC | GAG | GGC | TCA | ATG | AAC | TCC | GGC | GTG | GTC | CCA | GCC | TGT | 1056 |
| Ala | Leu | Pro | His<br>340 | Glu | Gly | Ser | Met | Asn<br>345 | Ser | Gly | Val | Val | Pro<br>350 | Ala | Cys | |
| GCA | CGT | TCG | ACC | CTG | TCG | GTG | GGG | GTG | TCG | GGA | ACC | CTG | GTG | CTG | CTC | 1104 |
| Ala | Arg | Ser<br>355 | Thr | Leu | Ser | Val | Gly<br>360 | Val | Ser | Gly | Thr | Leu<br>365 | Val | Leu | Leu | |
| CAA | GGG | GCC | CGG | GGC | TTT | GCC | TAA | | | | | | | | | 1128 |
| Gln | Gly | Ala | Arg<br>370 | Gly | Phe | Ala<br>375 | | | | | | | | | | |

( 2 ) INFORMATION FOR SEQ ID NO:2:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Glu | Arg | Ala | Ser<br>5 | Cys | Leu | Leu | Leu<br>10 | Leu | Leu | Pro | Leu | Val<br>15 | His |
| Val | Ser | Ala | Thr<br>20 | Thr | Pro | Glu | Pro<br>25 | Cys | Glu | Leu | Asp | Asp<br>30 | Glu | Asp |
| Arg | Cys | Val<br>35 | Cys | Asn | Phe | Ser | Glu<br>40 | Pro | Gln | Pro | Asp | Trp<br>45 | Ser | Glu | Ala |

-continued

| Phe | Gln | Cys | Val | Ser | Ala | Val | Glu | Val | Glu | Ile | His | Ala | Gly | Gly | Leu |
|  | 50 |  |  |  | 55 |  |  |  | 60 |  |  |  |  |  |  |

| Asn | Leu | Glu | Pro | Phe | Leu | Lys | Arg | Val | Asp | Ala | Asp | Arg | Asp | Pro | Arg |
| 65 |  |  |  |  | 70 |  |  |  | 75 |  |  |  |  |  | 80 |

| Gln | Tyr | Ala | Asp | Thr | Val | Lys | Ala | Leu | Arg | Val | Arg | Arg | Leu | Thr | Val |
|  |  |  |  | 85 |  |  |  |  | 90 |  |  |  |  | 95 |  |

| Gly | Ala | Ala | Gln | Val | Pro | Ala | Gln | Leu | Leu | Val | Gly | Ala | Leu | Arg | Val |
|  |  |  | 100 |  |  |  |  | 105 |  |  |  |  | 110 |  |  |

| Leu | Ala | Tyr | Ser | Arg | Leu | Lys | Glu | Leu | Thr | Leu | Glu | Asp | Leu | Lys | Ile |
|  |  | 115 |  |  |  |  | 120 |  |  |  |  | 125 |  |  |  |

| Thr | Gly | Thr | Met | Pro | Pro | Leu | Pro | Leu | Glu | Ala | Thr | Gly | Leu | Ala | Leu |
|  | 130 |  |  |  |  | 135 |  |  |  |  | 140 |  |  |  |  |

| Ser | Ser | Leu | Arg | Leu | Arg | Asn | Val | Ser | Trp | Ala | Thr | Gly | Arg | Ser | Trp |
| 145 |  |  |  |  | 150 |  |  |  |  | 155 |  |  |  |  | 160 |

| Leu | Ala | Glu | Leu | Gln | Gln | Trp | Leu | Lys | Pro | Gly | Leu | Lys | Val | Leu | Ser |
|  |  |  |  | 165 |  |  |  |  | 170 |  |  |  |  | 175 |  |

| Ile | Ala | Gln | Ala | His | Ser | Pro | Ala | Phe | Ser | Cys | Glu | Gln | Val | Arg | Ala |
|  |  |  | 180 |  |  |  |  | 185 |  |  |  |  | 190 |  |  |

| Phe | Pro | Ala | Leu | Thr | Ser | Leu | Asp | Leu | Ser | Asp | Asn | Pro | Gly | Leu | Gly |
|  |  | 195 |  |  |  |  | 200 |  |  |  |  | 205 |  |  |  |

| Glu | Arg | Gly | Leu | Met | Ala | Ala | Leu | Cys | Pro | His | Lys | Phe | Pro | Ala | Ile |
|  | 210 |  |  |  |  | 215 |  |  |  |  | 220 |  |  |  |  |

| Gln | Asn | Leu | Ala | Leu | Arg | Asn | Thr | Gly | Met | Glu | Thr | Pro | Thr | Gly | Val |
| 225 |  |  |  |  | 230 |  |  |  |  | 235 |  |  |  |  | 240 |

| Cys | Ala | Ala | Leu | Ala | Ala | Ala | Gly | Val | Gln | Pro | His | Ser | Leu | Asp | Leu |
|  |  |  |  | 245 |  |  |  |  | 250 |  |  |  |  | 255 |  |

| Ser | His | Asn | Ser | Leu | Arg | Ala | Thr | Val | Asn | Pro | Ser | Ala | Pro | Arg | Cys |
|  |  |  | 260 |  |  |  |  | 265 |  |  |  |  | 270 |  |  |

| Met | Trp | Ser | Ser | Ala | Leu | Asn | Ser | Leu | Asn | Leu | Ser | Phe | Ala | Gly | Leu |
|  |  | 275 |  |  |  |  | 280 |  |  |  |  | 285 |  |  |  |

| Glu | Gln | Val | Pro | Lys | Gly | Leu | Pro | Ala | Lys | Leu | Arg | Val | Leu | Asp | Leu |
|  | 290 |  |  |  |  | 295 |  |  |  |  | 300 |  |  |  |  |

| Ser | Cys | Asn | Arg | Leu | Asn | Arg | Ala | Pro | Gln | Pro | Asp | Glu | Leu | Pro | Glu |
| 305 |  |  |  |  | 310 |  |  |  |  | 315 |  |  |  |  | 320 |

| Val | Asp | Asn | Leu | Thr | Leu | Asp | Gly | Asn | Pro | Phe | Leu | Val | Pro | Gly | Thr |
|  |  |  |  | 325 |  |  |  |  | 330 |  |  |  |  | 335 |  |

| Ala | Leu | Pro | His | Glu | Gly | Ser | Met | Asn | Ser | Gly | Val | Val | Pro | Ala | Cys |
|  |  |  | 340 |  |  |  |  | 345 |  |  |  |  | 350 |  |  |

| Ala | Arg | Ser | Thr | Leu | Ser | Val | Gly | Val | Ser | Gly | Thr | Leu | Val | Leu | Leu |
|  |  | 355 |  |  |  |  | 360 |  |  |  |  | 365 |  |  |  |

| Gln | Gly | Ala | Arg | Gly | Phe | Ala |
|  | 370 |  |  |  |  | 375 |

( 2 ) INFORMATION FOR SEQ ID NO:3:

( i ) SEQUENCE CHARACTERISTICS:
    ( A ) LENGTH: 452 amino acids
    ( B ) TYPE: amino acid
    ( D ) TOPOLOGY: linear ( i i ) MOLECULE TYPE: protein ( x i ) SEQUENCE DESCRIPTION: SEQ ID NO:3:

| Ala | Asn | Pro | Gly | Leu | Val | Ala | Arg | Ile | Thr | Asp | Lys | Gly | Leu | Gln | Tyr |
| 1 |  |  |  | 5 |  |  |  |  | 10 |  |  |  |  | 15 |  |

| Ala | Ala | Gln | Glu | Gly | Leu | Leu | Ala | Leu | Gln | Ser | Glu | Leu | Leu | Arg | Ile |
|  |  |  | 20 |  |  |  |  | 25 |  |  |  |  | 30 |  |  |

| | | | | | | | | | | | | |
|---|---|---|---|---|---|---|---|---|---|---|---|---|
| Thr | Leu | Pro 35 | Asp | Phe | Thr | Gly | Asp 40 | Leu | Arg | Ile | Pro | His 45 | Val | Gly | Arg |
| Gly | Arg 50 | Tyr | Glu | Phe | His | Ser 55 | Leu | Asn | Ile | His | Ser 60 | Cys | Glu | Leu | Leu |
| His 65 | Ser | Ala | Leu | Arg | Pro 70 | Val | Pro | Gly | Gln | Gly 75 | Leu | Ser | Leu | Ser | Ile 80 |
| Ser | Asp | Ser | Ser | Ile 85 | Arg | Val | Gln | Gly | Arg 90 | Trp | Lys | Val | Arg | Lys 95 | Ser |
| Phe | Phe | Lys | Leu 100 | Gln | Gly | Ser | Phe | Asp 105 | Val | Ser | Val | Lys | Gly 110 | Ile | Ser |
| Ile | Ser | Val 115 | Asn | Leu | Leu | Leu | Gly 120 | Ser | Glu | Ser | Ser | Gly 125 | Arg | Pro | Thr |
| Gly | Tyr 130 | Cys | Leu | Ser | Cys | Ser 135 | Ser | Asp | Ile | Ala | Asp 140 | Val | Glu | Val | Asp |
| Met 145 | Ser | Gly | Asp | Ser | Gly 150 | Trp | Leu | Leu | Asn | Leu 155 | Phe | His | Asn | Gln | Ile 160 |
| Glu | Ser | Lys | Phe | Gln 165 | Lys | Val | Leu | Glu | Ser 170 | Arg | Ile | Cys | Glu | Met 175 | Ile |
| Gln | Lys | Ser | Val 180 | Ser | Ser | Asp | Leu | Gln 185 | Pro | Tyr | Leu | Gln | Thr 190 | Leu | Pro |
| Val | Thr | Thr 195 | Glu | Ile | Asp | Ser | Phe 200 | Ala | Asp | Ile | Asp | Tyr 205 | Ser | Leu | Val |
| Glu | Ala 210 | Pro | Arg | Ala | Thr | Ala 215 | Gln | Met | Leu | Glu | Val 220 | Met | Phe | Lys | Gly |
| Glu 225 | Ile | Phe | His | Arg | Asn 230 | His | Arg | Ser | Pro | Val 235 | Thr | Leu | Leu | Ala | Ala 240 |
| Val | Met | Ser | Leu | Pro 245 | Glu | Glu | His | Asn | Lys 250 | Met | Val | Tyr | Phe | Ala 255 | Ile |
| Ser | Asp | Tyr | Val 260 | Phe | Asn | Thr | Ala | Ser 265 | Leu | Val | Tyr | His | Glu 270 | Glu | Gly |
| Tyr | Leu | Asn 275 | Phe | Ser | Ile | Thr | Asp 280 | Asp | Met | Ile | Pro | Pro 285 | Asp | Ser | Asn |
| Ile | Arg 290 | Leu | Thr | Thr | Lys | Ser 295 | Phe | Arg | Pro | Phe | Val 300 | Pro | Arg | Leu | Ala |
| Arg 305 | Leu | Tyr | Pro | Asn | Met 310 | Asn | Leu | Glu | Leu | Gln 315 | Gly | Ser | Val | Pro | Ser 320 |
| Ala | Pro | Leu | Leu | Asn 325 | Phe | Ser | Pro | Gly | Asn 330 | Leu | Ser | Val | Asp | Pro 335 | Tyr |
| Met | Glu | Ile | Asp 340 | Ala | Phe | Val | Leu | Leu 345 | Pro | Ser | Ser | Ser | Lys 350 | Glu | Pro |
| Val | Phe | Arg 355 | Leu | Ser | Val | Ala | Thr 360 | Asn | Val | Ser | Ala | Thr 365 | Leu | Thr | Phe |
| Asn | Thr 370 | Ser | Lys | Ile | Thr | Gly 375 | Phe | Leu | Lys | Pro | Gly 380 | Lys | Val | Lys | Val |
| Glu 385 | Leu | Lys | Glu | Ser | Lys 390 | Val | Gly | Leu | Phe | Asn 395 | Ala | Glu | Leu | Leu | Glu 400 |
| Ala | Leu | Leu | Asn | Tyr 405 | Tyr | Ile | Leu | Asn | Thr 410 | Leu | Tyr | Pro | Lys | Phe 415 | Asn |
| Asp | Lys | Leu | Ala 420 | Glu | Gly | Phe | Pro | Leu 425 | Pro | Leu | Leu | Lys | Arg 430 | Val | Gln |
| Leu | Tyr | Asp 435 | Leu | Gly | Leu | Gln | Ile 440 | His | Lys | Asp | Phe | Leu 445 | Phe | Leu | Gly |
| Ala | Asn | Val | Gln | | | | | | | | | | | | |

450

(2) INFORMATION FOR SEQ ID NO:4:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO:4:

```
Thr Asn Pro Gly Leu Ile Thr Arg Ile Thr Asp Lys Gly Leu Glu Tyr
  1               5                  10                  15

Ala Ala Arg Glu Gly Leu Leu Ala Leu Gln Arg Lys Leu Leu Glu Val
             20                  25                  30

Thr Leu Pro Asp Ser Asp Gly Asp Phe Arg Ile Lys His Phe Gly Arg
         35                  40                  45

Ala Gln Tyr Lys Phe Tyr Ser Leu Lys Ile Pro Arg Phe Glu Leu Leu
     50                  55                  60

Arg Gly Thr Leu Arg Pro Leu Pro Gly Gln Gly Leu Ser Leu Asp Ile
 65                  70                  75                  80

Ser Asp Ala Tyr Ile His Val Arg Gly Ser Trp Lys Val Arg Lys Ala
                 85                  90                  95

Phe Leu Arg Leu Lys Asn Ser Phe Asp Leu Tyr Val Lys Gly Leu Thr
             100                 105                 110

Ile Ser Val His Leu Val Leu Gly Ser Glu Ser Ser Gly Arg Pro Thr
         115                 120                 125

Val Thr Thr Ser Ser Cys Ser Ser Asp Ile Gln Asn Val Glu Leu Asp
 130                 135                 140

Ile Glu Gly Asp Leu Glu Glu Leu Leu Asn Leu Leu Gln Ser Gln Ile
145                 150                 155                 160

Asp Ala Arg Leu Arg Glu Val Leu Glu Ser Lys Ile Cys Arg Gln Ile
             165                 170                 175

Glu Glu Ala Val Thr Ala His Leu Gln Pro Tyr Leu Gln Thr Leu Pro
         180                 185                 190

Val Thr Thr Gln Ile Asp Ser Phe Ala Gly Ile Asp Tyr Ser Leu Met
     195                 200                 205

Glu Ala Pro Arg Ala Thr Ala Gly Met Leu Asp Val Met Phe Lys Gly
 210                 215                 220

Glu Ile Phe Pro Leu Asp His Arg Ser Pro Val Asp Phe Leu Ala Pro
225                 230                 235                 240

Ala Met Asn Leu Pro Glu Ala His Ser Arg Met Val Tyr Phe Ser Ile
             245                 250                 255

Ser Asp Tyr Val Phe Asn Thr Ala Ser Leu Ala Tyr His Lys Ser Gly
         260                 265                 270

Tyr Trp Asn Phe Ser Ile Thr Asp Ala Met Val Pro Ala Asp Leu Asn
     275                 280                 285

Ile Arg Arg Thr Thr Lys Ser Phe Arg Pro Phe Val Pro Leu Leu Ala
 290                 295                 300

Asn Leu Tyr Pro Asn Met Asn Leu Glu Leu Gln Gly Thr Val Asn Ser
305                 310                 315                 320

Glu Gln Leu Val Asn Leu Ser Thr Glu Asn Leu Leu Glu Glu Pro Glu
             325                 330                 335

Met Asp Ile Glu Ala Leu Val Val Leu Pro Ser Ser Ala Arg Glu Pro
         340                 345                 350
```

```
        Val  Phe  Arg  Leu  Gly  Val  Ala  Thr  Asn  Val  Ser  Ala  Thr  Leu  Thr  Leu
                  355                      360                      365

Asn  Thr  Arg  Lys  Ile  Thr  Gly  Phe  Leu  Lys  Pro  Gly  Arg  Leu  Gln  Val
                  370                      375                      380

Glu  Leu  Lys  Glu  Ser  Lys  Val  Gly  Gly  Phe  Asn  Val  Glu  Leu  Leu  Glu
        385                      390                      395                      400

Ala  Leu  Leu  Asn  Tyr  Tyr  Ile  Leu  Asn  Asn  Leu  Tyr  Pro  Lys  Val  Asn
                            405                      410                      415

Glu  Lys  Leu  Ala  His  Arg  Phe  Pro  Leu  Pro  Leu  Leu  Arg  His  Ile  Gln
                            420                      425                      430

Leu  Tyr  Asp  Leu  Leu  Leu  Gln  Thr  His  Glu  Asn  Phe  Leu  Leu  Val  Gly
                       435                      440                      445

Ala  Asn  Ile  Gln  Tyr  Arg  Arg  Val
        450                           455
```

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( v ) FRAGMENT TYPE: N-terminal ( x i ) SEQUENCE DESCRIPTION: SEQ ID NO:5:

```
        Thr  Asn  Pro  Gly  Leu  Ile  Thr  Arg  Ile  Thr  Asp  Lys  Gly  Leu
        1                   5                        10
```

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:6:

```
        Lys  Val  Arg  Lys  Ala  Phe  Leu  Arg  Leu  Lys  Asn  Ser  Phe  Asp  Leu
        1                   5                        10                       15
```

( 2 ) INFORMATION FOR SEQ ID NO:7:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:7:

```
        Cys  Ser  Ser  Asp  Ile  Gln  Asn  Val  Glu  Leu  Asp  Ile  Glu  Gly  Asp  Leu
        1                   5                        10                       15

Glu  Glu  Leu  Leu  Asn  Leu  Leu  Gln  Ser  Gln  Ile  Asp  Ala  Arg  Leu  Arg
                       20                       25                       30

Glu  Val  Leu  Glu  Ser  Lys  Ile
                       35
```

( 2 ) INFORMATION FOR SEQ ID NO:8:

( i ) SEQUENCE CHARACTERISTICS:
  ( A ) LENGTH: 16 amino acids
  ( B ) TYPE: amino acid
  ( D ) TOPOLOGY: linear ( i i ) MOLECULE TYPE: protein ( v ) FRAGMENT TYPE: internal ( x i ) SEQUENCE DESCRIPTION: SEQ ID NO:8:

```
Leu Gln Pro Tyr Leu Gln Thr Leu Pro Val Thr Thr Gln Ile Asp Ser
1               5                   10                  15
```

( 2 ) INFORMATION FOR SEQ ID NO:9:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:9:

```
Gly Ile Asp Tyr Ser Leu Met Glu Ala Pro Arg Ala Thr Ala
1               5                   10
```

( 2 ) INFORMATION FOR SEQ ID NO:10:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:10:

```
Pro Ser Ser Ala Arg Glu Pro Val Phe Arg Leu Gly Val Ala Thr
1               5                   10                  15
```

( 2 ) INFORMATION FOR SEQ ID NO:11:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:11:

```
Ala Thr Leu Thr Leu Asn Thr Arg Lys Ile Thr
1               5                   10
```

( 2 ) INFORMATION FOR SEQ ID NO:12:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: protein ( v ) FRAGMENT TYPE: C-terminal ( x i ) SEQUENCE DESCRIPTION: SEQ ID NO:12:

| Gln | Thr | His | Glu | Asn | Phe | Leu | Leu | Val | Gly | Ala | Asn | Ile | Gln | Tyr | Arg |
| 1 | | | | 5 | | | | | 10 | | | | | 15 | |
| Arg | Val | | | | | | | | | | | | | | |

METHODS FOR IDENTIFYING INHIBITORS OF LPS-MEDIATED LBP BINDING

STATEMENT OF GOVERNMENT SUPPORT

This invention was made with the support of the United States Government, and the United States Government may have certain rights in the invention pursuant to the National Institutes of Health Contracts AI 25563 and AI 32021.

TECHNICAL FIELD

The present invention relates to a system and methods for identifying reagents which inhibit the interaction of lipopolysaccharide (LPS) binding to monocytes via LPS binding protein (LBP), and thereby inhibit sepsis.

BACKGROUND

Bacterial sepsis continues to be a major medical problem in patients with bacterial infections. The presence of bacterial endotoxin (lipopolysaccharide) in blood leads to marked hemodynamic, hematologic and metabolic changes that contribute to the septic shock syndrome in man and experimental animals. The physiological changes associated with sepsis are mediated by products released by direct LPS stimulation of cells of the monocytic lineage.

Recent work has established that LPS binds to the plasma protein LPS binding protein (LBP) forming high affinity complexes (LPS-LBP), that LBP is an opsonin for LPS-bearing particles, and that LPS-LBP complexes are the potent agonists for monocytic cells (MO) in septic shock syndrome. MAb to the MO plasma membrane protein, CD14, inhibit LBP dependent binding of LPS to MO and LPS-LBP dependent stimulation of cytokine release from MO. Thus, CD14, a plasma membrane protein present on all cells of monocytic lineage, mediates monocyte recognition of complexes of LPS and the plasma protein, LPS binding protein (LBP) leading to cytokine production during septic shock syndrome, Mathison, et al., *J. Immunol.*, 149:200 (1992); Wright, et al., *J. Exp. Med.*, 170:1231 (1989); Wright, et al., Science, 249:1431 (1990); Heumann, et al., *J. Immunol.*, 148:3505 (1992); and Lee, et al., *J. Exp. Med.*, 175:1697 (1992).

There is a need for a rapid and simple system for screening of large numbers of compounds for potential ability to inhibit binding of LPS to LBP and to inhibit binding interactions of LPS:LBP complex to CD14 on monocytes, in the development of therapeutic reagents for inhibition of septic shock and related LPS-mediated events.

BRIEF DESCRIPTION OF THE INVENTION

It has now been discovered that a rapid solution-phase screening assay can be performed to identify compounds that inhibit the binding of LPS to LBP or the binding of LPS:LBP complex to CD14 on monocytes. The assay is based on the observation that the fluorescence emissions of fluoresceinated LPS is dramatically effected when complexed with LBP to form LPS:LBP complex, and alternatively when the complex interacts with soluble CD14.

Thus, in one embodiment, the invention describes a method for identifying a compound which inhibits LPS binding LBP, which method comprises:

a) admixing putative inhibitory compounds in a binding reaction admixture that comprises fluoresceinated LPS and LBP; and b) measuring the fluorescence emitted by the binding reaction admixture, thereby identifying inhibitory activity of the compound.

Another embodiment of the invention describes a method for identifying a compound which inhibits LBP-dependent binding of LPS to monocyte receptor CD14, which method comprises:

a) admixing putative inhibitory compounds in a binding reaction admixture that comprises fluoresceinated LPS, LBP, and isolated CD14; and b) measuring the fluorescence emitted by the binding reaction admixture, thereby identifying inhibitory activity of the compound.

A related embodiment contemplates a kit for identifying a compound which inhibits LPS binding to LBP, which kit comprises, in an amount sufficient for at least one assay, fluoresceinated LPS and LBP.

A related kit embodiment contemplates a kit for identifying a compound which inhibits LBP-dependent binding of LPS to monocyte receptor CD14, which kit comprises, in an amount sufficient for at least one assay, fluoresceinated LPS, LBP, and isolated CD14.

Other related embodiments will be apparent based on the disclosures contained herein.

BRIEF DESCRIPTION OF THE DRAWINGS

In the drawings forming a portion of this disclosure.

DETAILED DESCRIPTION OF THE INVENTION

A. Definitions

Figure 1:
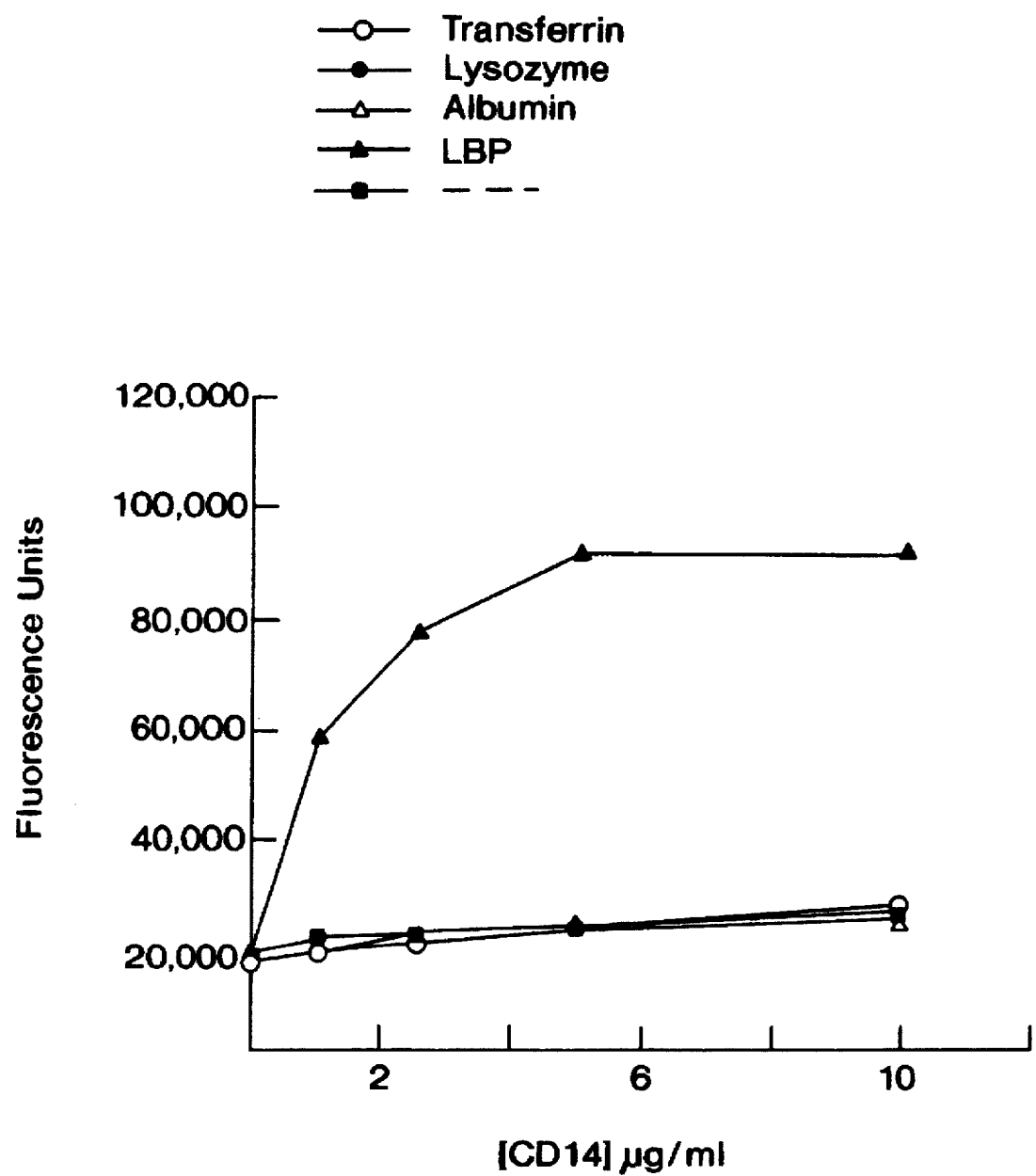
FIG. 1 illustrates the dose-response curve of the enhanced fluorescence intensity resulting from the LBP-mediated binding of F-LPS to CD14 in a soluble binding assay measured spectrophotometrically as described in Example 1. Fluorescence units are plotted on the Y-axis against increasing concentrations of added CD14 ranging from 0 to 10 micrograms/milliliter (ug/ml) on the X-axis. Other LPS-binding proteins had no measurable effect on increasing the (FI) of F-LPS to CD14 throughout the tested concentrations of CD14.

"Amino acid residue" refers to an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. 1.822(b) (2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b) (4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

B. Methods for Identifying Inhibitors of LBP-Dependent LPS-Mediated Activation of Cell Surface CD14

1. General Methods

The invention describes screening methods for the identification of compounds which inhibit the binding and cell-activation interactions between LPS and LBP, and for the identification of compounds which inhibit the interactions between LPS:LBP complex and the monocyte's surface receptor CD14.

The basic method for identifying a compound which inhibits lipopolysaccharide (LPS) binding to LPS binding protein (LBP) comprises the steps of:

a) admixing a candidate inhibitory compound in a binding reaction admixture that comprises:
  i) fluoresceinated LPS, and
  ii) LBP; and
b) measuring the fluorescence emitted by the binding reaction admixture, thereby identifying said inhibition activity of the compound.

A related assay method includes the additional reagent of soluble CD14, and allows for the identification of compounds which inhibit LBP-dependent binding of LPS to monocyte receptor CD14.

Thus, a method is also contemplated for identifying a compound which inhibits LBP-dependent binding of LPS to monocyte receptor CD14, which method comprises:

a) admixing a candidate compound in a binding reaction admixture that comprises:
  i) fluoresceinated LPS,
  ii) LBP, and
  iii) isolated CD14; and
b) measuring the fluorescence emitted by the binding reaction admixture, thereby identifying the inhibition activity of the candidate compound.

As described in the Examples, the amount of fluorescent emissions detectable in such a binding reaction admixture is markedly dependent upon the interaction between the labeled LPS and LBP or on the interaction of the LPS:LBP complex with CD14. Thus, the assay provides a sensitive measure for compounds having the desired inhibitory activity.

A binding reaction admixture is an aqueous solution having suitable pH, buffers and ionic strength as to be compatible with the dissolution of the added reagents and to support the binding interaction and the attendant fluorescent emissions. The constituents of the binding reaction admixture other than the specified LPS, LBP and CD14 are not critical to the invention in that any number and amount of buffers, salts and macromolecules may be included as desired and compatible in the admixture without detracting from the basic invention. Exemplary buffers include phosphate buffered saline, HEPES, TRIS and the like physiological buffers, typically buffered to physiological pH, or in the range of about 6.5–8.0, preferably about 7.0–7.5.

The essential reagent components for a binding reaction admixture are described in more detail herein below.

The resulting binding interactions between LPS and LBP to form the LPS:LBP complex and between LPS:LBP complex and CD14 is detected by changes in the amount of fluorescence or by changes in fluorescence properties in the assay. Inhibition of binding interactions by candidate inhibitor compounds can readily be measured by standard fluorometers capable of detecting changes in fluorescence intensity (FI) or other changes in fluorescent properties in the assay as described further herein.

The choice of fluorescent label upon the LPS molecule can vary so long as it is conveniently linked to the LPS in a manner that maintains its fluorescent properties. Of particular importance is the use of a fluorescent label which is capable of self-quenching such that the upon LPS binding to LBP or upon LPS:LBP complex interactions with CD14 the quenching activity is reduced, indicating interactions between LPS and the other components of the assay. Typical fluorescent labels include fluorescein and the like fluorescent labels. Suitable fluorescent labels are readily available through a variety of commercial vendors including the fluorescent labels described in "Handbook of Fluorescent Probes and Research Chemicals", ed. by R. P. Haugland, Molecular Probes, publisher, Eugene, Oreg. (1989–1991 and 1992–1993), and available from (Molecular Probes, Eugene Oreg.).

Particularly preferred and exemplary is fluorescein isothiocyanate, which is commercially available from a variety of commercial sources including Molecular Probes.

The quantitative measurement of fluorescent emissions spectrum and/or intensity from a binding reaction admixture can be accomplished by a variety of means as is well known, including manual and automated methods. The fluorimetric measurement methods are not to be construed as limiting to the present invention. Preferred are automated fluorometers designed to rapidly measure fluorescence of multiple samples to facilitate statistically significant measurement and to facilitate the measurement of multiple candidate inhibitory compounds. Exemplary fluorometers and spectrofluorometers suitable for the present methods are available from Perkin-Elmer, Hewlett-Packard, Hitachi, SLM and the like commercial vendors. Particularly preferred is the SLM 8000 photon counting spectrofluorimeter available from SLM (Urbana, Ill.).

By the application of the present methods, useful inhibitory compounds are identified that may be used in vitro and/or in vivo. Insofar as the method has broad utility as a screening method, it is appreciated that many new inhibitory compounds can be identified. Therefore, the present invention also contemplates the product identified by the present screening methods.

2. Fluoresceinated Lipopolysaccharides

Lipopolysaccharides (LPS) are a complex family of bacterial endotoxin macromolecules whose structure varies depending upon the bacterial source of the LPS. However, LPS molecules as a class share common features including a lipid-A binding region that participates in the binding interaction with LBP to form the LPS:LBP complex, and binds to CD14. Thus, any LPS or lipid-A molecule can be utilized in the present assay so long as it can be fluorescently labeled and retain the capacity to bind LBP, to form LPS:LBP complexes, and to bind CD14.

Preferred LPS molecules are obtained from any gram negative bacteria as is well known. Particularly preferred is Re595 LPS that is purified from lyophilized *Salmonella minnesota* as described by Galanos et al., *Eur. J Biochem.*, 9:245–249 (1969). Re595 LPS and other candidate LPS molecules can be obtained from a variety of commercial sources, including LIST Biological (Campbell, Calif.).

The conjugation of a fluorescent label to a LPS molecule used in the present methods can be conducted by a variety of means, and need not be considered as limiting. A preferred fluorescent LPS is fluoresceinated Re595 LPS (F-LPS). Re595 was fluoresceinated with fluorescein isothiocyanate by the methods of Skelly et al., *Infect. Immunol.*, 23:287–293 (1979), and as described in the Examples.

LPS can be present in a binding reaction admixture for the present methods in amounts sufficient to measurably detect enhanced fluorescence in the presence of LBP, as described herein. Preferably the admixture contains at least from about 1 nanogram (ng) to about 100 ng of LPS per milliliter (ng/ml) of admixture, and more preferably about 10 ng/ml.

3. LPS Binding Protein

LPS binding protein (LBP) has been extensively characterized and is present in a variety of mammalian species. LBP is present in the serum of mammals and is known to participate in LPS-dependent cell activation, as described herein.

LBP is highly conserved across species, and has been purified and sequenced from a variety of species, including human and rabbit LBP. See, for example Schuman et al., *Science*, 249:1429–1431 (1990). The amino acid residue sequence of human and rabbit (lapine) LBP is also shown in SEQ ID NOs 3 and 4, respectively.

Thus, due to the conservation among species, any mammalian LBP can be utilized in the present invention so long as it is in a substantially isolated form. By substantially isolated is meant that the protein preparation contains at least 10%, preferably 50%, and more preferably at least about 95% homogeneous LBP by weight of total isolated LBP composition.

The purification of LBP from acute phase serum can be accomplished from any mammalian species according to the teachings of Tobias et al., *J. Exp. Med.*, 164:777–793 (1986), and Schuman et al., *Science*, 249:1429–1431 (1990), the teachings of which are incorporated by reference. Equivalent purification methods can readily be applied to the isolation of LBP from acute phase serum of other mammalian species.

LBP can be present in a binding reaction admixture for the present methods in amounts sufficient to measurably detect enhanced fluorescence in the presence of fluoresceinated LPS, as described herein. Preferably the admixture contains at least from about 1 nanogram (ng) to about 1000 ng of LBP per milliliter (ng/ml) of admixture, and more preferably about 40 ng/ml.

4. Isolated CD14

CD14, a macrophage/polymorphonuclear leukocyte differentiation antigen, has been reported to bind LPS in the presence of LBP. See, Wright et al., *Science*, 249:1431–1433 (1990); Couturier et al., *J. Immunol.*, 147:1899–1904 (1991); Heumann et al., *J. Immunol.*, 148:3505–3511 (1992); Kitchens et al., *J. Exp. Med.*, 176:485–494 (1992) and Lee et al., *J. Exp. Med.*, 175:1697–1705 (1992). LPS binding to CD14 results in activation of cellular responses.

Monocyte cell receptor CD14 has been extensively characterized and is present in a variety of mammalian species. The cDNA coding CD14 and its deduced amino acid residue sequence are well known in the art. See Goyert et al., *Science*, 239:497–500 (1988); Ferrero et al., *Nuc. Acids Res.*, 16:4173 (1988); and Bazil et al., *Eur. J. Immunol.*, 16:1583–1589 (1986). Human CD14 was cloned from a human monocytic cell line (HL-60) as described in *Blood*, 73:284 (1989). The amino acid residue sequence of a preferred isolated human CD14 is shown in SEQ ID NO 2. In addition, the nucleotide sequence that codes for the amino acid residue sequence of human CD14 is shown in SEQ ID NO 1.

Any mammalian CD14 can be utilized in the present invention, so long as it is in a substantially isolated form. By substantially isolated is meant that the protein preparation contains at least 10%, preferably 50%, and more preferably at least about 95% homogeneous CD14 by weight of total isolated CD14 composition. A preferred CD14 for use in the invention is human CD14.

CD14 can be present in a binding reaction admixture for the present methods in amounts sufficient to measurably detect enhanced fluorescence in the presence of LBP and LPS, as described herein. Preferably the admixture contains at least from about 1 microgram (ug) to about 50 ug, preferably about 5 to 30 ug, of CD14 per milliliter (ug/ml) of admixture, and more preferably about 10 ug/ml.

A preferred CD14 is in the form of soluble CD14. Soluble CD14 has been described by Bazil et al., *Eur. J. Immunol.*, 16:1583 (1989); Bazil et al., *Mol. Immunol.*, 26:657–662 (1989); and is described herein.

Isolated human CD14 can be prepared from a variety of sources, including isolation from human serum as described by Bazil et al., *Eur. J. Immunol.*, 16:1583 (1989), and isolation from urine of nephritic patients as described by Bazil et al., *Mol. Immunol.*, 26:657–662 (1989), the teachings of which are hereby incorporated by reference. CD14 can also be prepared by recombinant DNA methods.

Compositions containing CD14 can be further enriched for CD14 using an affinity chromatography column composed of commercially available anti-CD14 antibody, such as monoclonal antibody 63D3, available from the American Type Culture Collection (ATCC No. HB 44). Alternatively, CD14 can be prepared from monocytes or other cells that contain cell surface CD14 by culturing the cells and harvesting the CD14 molecules released into the culture medium. Release of cellular CD14 can be enhanced by the use of enzymes that specifically cleave the membrane anchor of CD14, also referred to as a GPI tail. Cleavage of a GPI tail can be accomplished by the use of phosphotidyl inositol phospholipase C as described by Bazil et al., *Mol. Immunol.*, 26:657–662 (1989).

Alternatively, CD14 can be produced by recombinant DNA (rDNA) methods as described herein using a rDNA molecule that codes for a CD14 protein and is present in a DNA expression vector capable of expressing the CD14 protein. A preferred recombinant CD14 protein is encoded by the nucleic acid sequence shown in SEQ ID NO 1.

DNA segments (i.e., synthetic oligonucleotides) that encode CD14 can easily be synthesized by chemical techniques, for example, the phosphotriester method of Matteucci, et al., (*J. Am. Chem. Soc.*, 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

Furthermore, DNA segments consisting essentially of structural genes encoding a CD14 protein can be obtained from recombinant DNA molecules containing a gene that defines CD14.

As used herein, the term "vector" refers to a DNA molecule capable of autonomous replication in a cell and to which another DNA segment can be operatively linked so as to bring about replication of the attached segment. A vector capable of directing the expression of a CD14 gene is referred to herein as an "expression vector". Thus, a recombinant DNA molecule is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the CD14 structural gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the CD14 gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, are particularly preferred for use as a recombinant DNA molecule of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the pEE14 vector from Celltech described herein, and the like eucaryotic expression vectors.

In preferred embodiments, the eucaryotic cell expression vectors used to construct the recombinant DNA molecules of the present invention include a selection marker that is effective in a eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982). Alternatively, the selectable marker can be present on a separate plasmid, and the two vectors are introduced by co-transfection of the host cell, and selected by culturing in the appropriate drug for the selectable marker.

The invention also contemplates a host cell transformed with a recombinant DNA molecule of the present invention. The host cell can be either procaryotic or eucaryotic, although eucaryotic cells are preferred. Eucaryotic cells useful for expression of a CD14 protein are not limited, so long as the cell line is compatible with cell culture methods and compatible with the propagation of the expression vector and expression of the CD14 gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eucaryotic tissue culture cell lines. Particularly preferred and exemplary is the CHO cell line described herein.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982).

With regard to transformation of vertebrate cells with vectors containing rDNAs, see, for example, Graham et al., *Virol.*, 52:456 (1973); Wigler et al., *Proc. Natl. Acad. Sci. USA*, 76:1373–76 (1979), and the teachings herein.

Successfully transformed cells, i.e., cells that contain a rDNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of CD14, or by the detection of the biological activity of CD14.

For example, cells successfully transformed with an expression vector produce proteins displaying CD14 antigenicity or biological activity. Samples of cells suspected of being transformed are harvested and assayed for either CD14 biological activity or antigenicity.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying CD14 antigenicity or biologically activity.

Nutrient media useful for culturing transformed host cells are well known in the art and can be obtained from several commercial sources. In embodiments wherein the host cell is mammalian, a "serum-free" medium can be used. Preferred is the culturing conditions described herein.

C. Screening Kits

The present invention also describes a system, in kit form, for identifying a compound which inhibits lipopolysaccharide (LPS) binding to lipopolysaccharide binding protein (LBP) and in a related embodiment describes a kit for identifying a compound which inhibits LPS:LBP complex interactions with monocyte receptor CD14.

In the first embodiment, the kit comprises, in an amount for at least one assay, fluoresceinated LPS and LBP.

In a second embodiment, the kit comprises, in an amount for at least one assay, fluoresceinated LPS, LBP and isolated CD14 where interactions with CD14 are to be measured.

A kit system of the invention typically includes, the fluoresceinated LPS and LBP as separately packaged reagents. The related system preferably also contains isolated CD14 as a separately packaged reagent.

Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

A diagnostic system of the present invention can also include a one or more of the other reagents used for a screening assay as described herein, in an amount sufficient for at least one assay.

The reagent species of any screening system described herein can be provided in solution, as a liquid dispersion or as a substantially dry power, e.g., in lyophilized form. A solid support such as the before-described microtiter plate and one or more buffers can also be included as separately packaged elements in this assay system.

The packaging materials discussed herein in relation to screening systems are those customarily utilized in diagnostic systems, and can be formulated for single assay use, multiple assay use, manual or automated assay protocols, and the like.

The term "package" refers to a solid matrix or material such as glass, plastic (e.g., polyethylene, polypropylene and polycarbonate), paper, foil and the like capable of holding within fixed limits a diagnostic reagent such as the fluoresceinated LPS, LBP, CD14 and/or detergents and assay buffers. Thus, for example, a package can be a bottle, vial, plastic and plastic-foil laminated envelope or the like container used to contain a contemplated assay method reagent.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a polypeptide or antibody composition of the invention. The kit may also have containers containing any of the other above-recited reagents used to practice the methods.

D. Compounds Which Inhibit LBP-Dependent LPS Binding to CD14

By the methods of the present invention, numerous compounds are identified which inhibit LPS binding to LBP and/or which inhibit LBP-dependent LPS binding to CD14. These compounds include but are not limited to polypeptides and antibodies as described further herein.

1. Polypeptides

Inhibitory polypeptides include those which have amino acid residue sequence functionally similar to (1) the LPS-binding site on LBP, (2) the LPS-binding site on CD14, (3) the CD14-binding site on LBP or (4) the LBP-binding site on CD14.

Polypeptides are "functionally similar" in this context where the polypeptide has a sequence derived from a binding site on a preselected protein and binds to the appropriate ligand in the present binding assay. Thus, for example, a polypeptide is functionally similar to the LPS-binding site on LBP where its amino acid sequence is derived from a LBP sequence and it inhibits LPS binding to LBP.

Thus, a polypeptide functionally similar to the LPS-binding site on LBP has a amino acid residue sequence that corresponds to the sequence of the portion of LBP that participates in binding to LPS. Similarly, the CD14-binding site on LBP has a amino acid residue sequence that corresponds to the sequence of the portion of LBP that participates in binding to CD14.

Exemplary polypeptides for use in the present invention that are derived from rabbit LBP are shown in Table 1.

TABLE 1

| # | SEQ ID NO | Amino Acid Residue Sequence |
|---|---|---|
| 2 | 6 | KVRKAFLRLKNSFDL |
| 3 | 7 | CSSDIQNVELDIEGDLEELLNLLQSQIDARLREVLESKI |
| 6 | 10 | PSSAREPVFRLGVAT |
| 7 | 11 | ATLTLNTRKIT |

The binding sites defined by the polypeptides shown in Table 1 present on LBP are biologically active as demonstrated by the data for Peptides 2, 3, 6 and 7 shown in Examples 1 and 2. The binding sites defined by these peptides are also found on the human LBP protein at the same amino acid residue position numbers. The human LBP sequence is shown in SEQ ID NO 3. The invention therefor contemplates polypeptides which includes an LBP binding site that corresponds to any mammalian LBP binding site and that which is aligned on LBP at the site defined by the above rabbit LBP polypeptides.

Thus, in one embodiment, the invention contemplates a polypeptide of about 10 to about 100 amino acid residues in length that includes an amino acid residue sequence which defines an LBP binding site according to the present invention. Preferably, the included binding site sequence corresponds to the sequence of a mammalian LBP. More preferably, a polypeptide includes a sequence shown in Table 1, or its human counterpart sequence shown in SEQ ID NO 3.

In one embodiment, it is preferred that the polypeptide consist essentially of an LBP sequence and include the above-recited rabbit or human binding site sequence. More preferably, a polypeptide of this invention consist essentially of a sequence shown in Table 1, or its human counterpart.

2. Antibody Compositions

In another embodiment, the invention contemplates antibody molecules, including monoclonal antibodies and biologically active fragments thereof, which are inhibitory in the present screening methods. Such inhibitory antibodies are deemed useful for in vitro and/or in vivo inhibition of LPS binding to LBP or LPS-mediated monocyte activation.

A useful antibody immunoreacts with either LBP of CD14 and exhibits inhibition activity in a screening method of this invention.

Preferred anti-LBP antibody molecules are the monoclonal antibodies (Mabs) 2B5, 18G4, 1E5 and 8F5. Preferred anti-CD14 antibodies are the Mabs 28C5, 5G3, 4F2, 13A7, 10B7 and 26F3. These antibodies, and their preparation are described further herein.

E. Therapeutic Compositions

Insofar as the present invention also contemplates therapeutic uses of an identified inhibitor of this invention, therapeutic compositions useful for practicing the therapeutic methods are also contemplated. Therapeutic compositions of the present invention contain a physiologically tolerable carrier together with at least one species of inhibitor as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Particularly preferred are phospholipid and liposome compositions as described herein. In addition, a therapeutic amount of an inhibitor can be present in a ointment or on a diffusible patch, such as a bandage, as to afford local delivery of the agent.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein. Exemplary of such additional liquid phases are glycerin, vegetable oils such as cottonseed oil, organic esters such as ethyl oleate, and water-oil emulsions, particularly the liposome compositions described earlier.

A therapeutic composition contains an effective amount of an inhibitor of the present invention, typically an amount of at least 0.1 weight percent of active inhibitor per weight of total therapeutic composition. A weight percent is a ratio by weight of inhibitor to total composition. Thus, for example, 0.1 weight percent is 0.1 grams of inhibitor per 100 grams of total composition.

F. Therapeutic Methods

An inhibitor compound identified by the present methods can be used therapeutically to inhibit LBP-dependent binding of LPS to monocytes via CD14, and thereby inhibit the events attendant to the binding of LPS to monocytes, including monocyte activation and septic shock.

Thus, the invention also contemplates a method for inhibiting LBP-dependent binding of LPS to CD14, and comprises contacting, in vivo or in vitro, a therapeutic inhibitor composition identified by the methods of this invention with cells that contain CD14. In one embodiment, the contacting in vivo is accomplished by administering a therapeutically effective amount of a physiologically tolerable composition containing an inhibitor compound of this invention to a patient, thereby contacting the CD14-containing cells present in the patient.

Thus, the present invention describes in one embodiment a method for inhibiting septic shock in a human comprising administering to the human an immunotherapeutically effective amount of the inhibitor composition of this invention.

A representative patient for practicing the present methods is any human at risk for monocyte activation and septic shock. A therapeutically effective amount of an inhibitor compound is a predetermined amount calculated to achieve the desired effect, i.e., to inhibit the LBP-dependent binding of LPS to CD14 present on monocytes in the patient, and thereby decrease the likelihood of monocyte activation in the patient. In the case of in vivo therapies, an effective amount can be measured by improvements in one or more symptoms associated with monocyte activation.

Thus, the dosage ranges for the administration of a compound of the invention are those large enough to produce the desired effect in which the symptoms of septic shock and monocyte activation are ameliorated or the likelihood of activation are decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an inhibitor compound of this invention is typically an amount such that when administered in a physiologically tolerable composition is sufficient to achieve a plasma or local concentration of from about 100 picomolar (pM) to 100 nanomolar (nM), preferably about 1 to 50 nM, and most preferably about 10 to 30 nM.

The inhibitor compound of the invention can be administered parenterally by injection or by gradual infusion over time. The compound can be administered intravenously, intraperitoneally, intramuscularly, subcutaneously, intracavity, transdermally, dermally, and can be delivered by peristalic means.

The therapeutic compositions containing an inhibitor compound of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Fluorescence Spectroscopy Assay System for Measuring the Binding of Lipopolysaccharide (LPS) to LPS-Binding Protein (LBP)

The fluorescence spectroscopy assay method detects the intensity of fluorescence of fluoresceinated LPS in the presence of LBP.

A. Preparation of Fluoresceinated LPS

LPS was purified from lyophilized *Salmonella minnesota* Re595 bacteria by well known methods as described by Galanos et al., *Eur. J. Biochem.*, 9:245–249 (1969), the teachings of which are hereby incorporated by reference. The resultant purified LPS was designated Re595 LPS. To produce a fluorescently labeled Re595 LPS (F-LPS), fluorescein isothiocyanate was reacted with the isolated Re595 LPS according to standard labeling methods as described by Skelly et al., *Infect. Immunol.*, 23:287–293 (1979).

B. Preparation of LBP

Rabbit lipoprotein binding protein (LBP) was isolated from acute phase rabbit serum as described by Tobias et al., *J. Exp. Med.*, 164:777–793 (1986). Briefly, rabbit LBP was prepared using a two step chromatographic procedure.

Serum was obtained from a rabbit in acute phase following standard serum isolation methods. The serum was first fractionated on Bio Rex-70 resin (Bio-Rad Laboratories, Richmond, Calif.) equilibrated with 41 mM NaCl in 50 mM phosphate buffer, pH 7.3, containing 2 mM EDTA, washed with equilibration buffer, and eluted with a linear gradient of 220 to 500 mM NaCl in the same buffer. Fractions were collected, assayed for LBP and pooled. The pooled fractions were then fractionated on HPLC (Perkin-Elmer, Norwalk, Conn.) with a Mono-Q column (Pharmacia, Piscataway, N.J.) that was equilibrated with 2 mM diethanolamine buffer, pH 8.3, and eluted with a first gradient of 0–50 mM ammonium sulfate in 20 mM diethanolamine, pH 8.3, and then a second gradient of 50–333 mM ammonium sulfate in the same buffer. Fractions were collected, assayed for LBP and pooled to form purified LBP. Purification is typically about 2,000 fold over serum, and acute phase serum is observed to contain about 30–35 ug LBP per ml of serum.

C. Polypeptide Synthesis

Polypeptides were synthesized using t-boc chemistry on a resin in automated chemical solid-phase synthesis with ABI 430A and ABI 431A peptide synthesizers commercially available from Applied Biosystems. After synthesis the peptides were released from the resin using hydrogen fluoride and purified by HPLC. The polypeptides have a sequence derived from the sequence of rabbit LBP shown in SEQ ID NO 3. The sequence of the polypeptides prepared and used in the present assay methods are described in Table 2.

TABLE 2

| # | SEQ ID NO | Amino Acid Residue Sequence |
|---|---|---|
| 1 | 5 | TNPGLITRITDKGL |
| 2 | 6 | KVRKAFLRLKNSFDL |
| 3 | 7 | CSSDIQNVELDIEGDLEELLNLLQSQIDARLREVLESKI |
| 4 | 8 | LQPYLQTLPVTTQIDS |
| 5 | 9 | GIDYSLMEAPRATA |
| 6 | 10 | PSSAREPVFRLGVAT |
| 7 | 11 | AILILNTRKIT |
| 8 | 12 | QTHENFLLVGANIQYRRV |

In Tables 1 and 2, "#" denotes the Peptide number. The correspondence of the peptides shown in Tables 1 and 2 to residue position numbers shown in SEQ ID NO 4 are as follows: Peptide 1 (1–14); Peptide 2 (92–106); Peptide 3 (134–172); Peptide 4 (184–199); Peptide 5 (202–215); Peptide 6 (346–360); Peptide 7 (364–374); and Peptide 8 (439–456).

D. Assay Method

The assay method of this invention is based on the observation that LBP increases the fluorescence intensity (FI) of F-LPS in solution which involves a change in the aggregate size of LPS and provides an indication of the interaction between LBP and LPS. The assay reaction admixture was prepared by admixing 10 ng/ml F-LPS and 1 ug/ml rabbit LBP into a solution of phosphate buffered saline (PBS) containing 2 mM EDTA, pH 7.4. The FI was then measured with an SLM 8000 photon counting spectrophotometer (SLM, Urbana, Ill.). A continuous FI output was measured over time while first the F-LPS was added to the PBS/EDTA solution, and then the LBP was added.

Baseline fluorescence in arbitrary units of about 100 FI units (FIU) was observed in the absence of F-LPS. Upon addition of F-LPS, the FI value typically increased to about 700–900 FIU within 5 seconds. Upon addition of the LBP, the FI increased to 2300–2700 FIU within about 5–50 seconds, and remained stable for over 150 seconds. Thus, it was observed that the addition of LBP substantially increased the FI of F-LPS.

To study the effect of an LBP-derived polypeptide upon the effect of LBP on the FI of F-LPS, a polypeptide was added to the assay admixture at a concentration of 1 mM polypeptide prior to the addition of LBP, which was typically added about 30 to 150 seconds after the polypeptide was added to the admixture. Peptides 1–8, whose sequences are shown in Table 2, were each separately added to assay reaction admixtures, and the resulting FI was measured. The effect upon FI is shown in Table 3.

TABLE 3

| Polypeptide | +F-LPS | +peptide | +LBP |
| --- | --- | --- | --- |
| Experiment A | | | |
| none | 900 | n.a. | 2700 |
| 1 | 900 | 900 | 2400 |
| 2 | 900 | 800 | 800 |
| 3 | 800 | 1300 | 2100 |
| 4 | 800 | 900 | 2300 |
| Experiment B | | | |
| none | 750 | n.a. | 2300 |
| 5 | 750 | 750 | 2000 |
| 6 | 750 | 800 | 1500 |
| 7 | 800 | 1600 | 1300 |
| 8 | 700 | 800 | 2300 |

The data in Table 3 is reported as fluorescence intensity units (FIU) obtained in the presence of F-LPS alone (+F-LPS), F-LPS+peptide (+peptide) or F-LPS+peptide+LBP (+LBP), as described in Example 1. "n.a." indicates not applicable because no peptide was added.

The data in Table 3 indicates that several of the polypeptides tested substantially reduced the detectable FI from F-LPS and therefore inhibited LPS binding to LBP in the assay. In particular, peptides 2, 6 and 7 strongly inhibit fluorescence of F-LPS and therefore strongly inhibit LPS binding to LBP. Peptide 3 appears to weakly inhibit LPS binding to LBP.

2. Fluorescence Spectroscopy Assay System for Measuring the Binding of Lipopolysaccharide (LPS) to Human CD14

The fluorescence spectroscopy assay method also detects the intensity of fluorescence of fluoresceinated LPS in the presence of LBP and soluble CD14.

A. Preparation of CD14

For the preparation of soluble CD14, Chinese Hamster Ovary (CHO) cells were first transfected with an expression vector containing cDNA encoding human CD14. A soluble form of human CD14 was isolated by immunoaffinity chromatography from tissue culture medium of human CD14 cDNA-transfected CHO cells. The transfection was accomplished by cloning a full length human CD14 cDNA as described in Blood, 73:284 (1989), incorporated herein by reference.

To that end, human CD14 cDNA was cloned from a human monocytic cell line (HL-60) (American Type Culture Collection, ATCC No. 240) using standard cDNa cloning methods, the isolated human CD14 cDNA nucleic acid molecule was cloned into the mammalian expression vector pEE14 (Celltech), and the expression vector was introduced into CHO cells for expression of human CD14. The pEE14 vector has an inducible glutamine synthetase gene (GS) which was used to express the cDNA encoding the CD14 gene. The full-length DNA sequence of the cDNA molecule encoding human CD14 is shown in SEQ ID NO 1. Cells expressing soluble CD14 were identified using an ELISA assay by reactivity with commercially available anti-CD14 mAb 63D3 (ATCC No. HB 44).

One clone, identified as 523, was demonstrated to express both soluble CD14 in the cell culture supernatant and a membrane-associated form which could be detected by FACS analysis. The soluble form of clone 523 was determined to be N-terminally processed at amino acid residue 20 of the predicted translated protein sequence. It was determined by C-terminal sequence analysis of the soluble CD14 that the C-terminus of the protein was intact; no processing had occurred which was similar to that noted in the soluble CD14 isolated from human serum (Bazil, et al., Eur. J. Immunol., 16:1583 (1986). The soluble CD14 isolated from urine of nephritic patients is lacking the eight most C-terminal amino acids (Bazil et al., Mol. Immunol., 26:657 (1989). The soluble CD14 expressed by clone 523 is believed to have avoided the processing steps at the C-terminus as a consequence of its expression in CHO cells.

Purification of the soluble CD14 was accomplished thereafter by purifying the expressed protein from the CHO cell culture supernatants on an affinity column composed of commercially available mAb 63D3 obtainable from the American Type Culture Collection (ATCC No. HB 44).

B. Assay Method

The assay to measure binding interactions between CD14 and LPS or LPS-LBP complex was conducted essentially as described in Example 1 with the following exceptions. First, the amount of rabbit LBP in the reaction admixture was 40 ng/ml. Second, soluble CD14 (sCD14) prepared as described in Example 2A was added to the reaction admixture at a concentration of 10 ug/ml prior to addition of the LBP to the reaction admixture. Peptides 6, 7 and 8, whose sequences are shown in Table 2, were each separately added to assay reaction admixtures, and the resulting FI was measured. The effect upon FI is shown in Table 4.

TABLE 4

| Polypeptide | +F-LPS | +peptide | +CD14 | +LBP |
| --- | --- | --- | --- | --- |
| none | 1400 | n.a. | 1500 | 6300 |
| 6 | 1200 | 1300 | 1300 | 3500 |
| 7 | 1200 | 2400 | 2000 | 1500 |
| 8 | 1400 | 1400 | 1500 | 5400 |

The data is reported as described in the legend to Table 3 except that "+CD14" indicates admixture of F-LPS+peptide+CD14+LBP, as described in Example 2.

The data in Table 4 indicates first, in the absence of polypeptide, that the presence of CD14 does not interfere with the assay and strong FI is detectable. The data further indicates that several of the polypeptides tested substantially reduced the FI detectable on F-LPS in the presence of LBP and CD14 and therefore those polypeptides are characterized as inhibiting LPS binding to LBP or CD14 in the assay. In particular, peptides 6 and 7 strongly inhibit fluorescence of F-LPS and therefore strongly inhibit LPS binding to LBP.

The FI effects via the binding of F-LPS to LBP were also compared in the present assay with other proteins shown to bind LPS including human serum albumin (HSA), apotransferrin, lysozyme, and bactericidal-permeability increasing protein (BPI) in place of polypeptide. For the assay, LBP or the other known LPS-binding proteins were added to the admixture at a concentration of 300 nanograms/milliliter (ng/ml) and were separately admixed with varying amounts the recombinant human soluble CD14 ranging in concentration from 0 to 10 micrograms/milliliter (ug/ml).

To this admixture, 20 ng/ml of F-LPS prepared in Example 1 were admixed to form a binding admixture. Fluorescence measurements were then performed as described above to determine the effect of LBP and CD14 on the FI of F-LPS.

Figure 2:
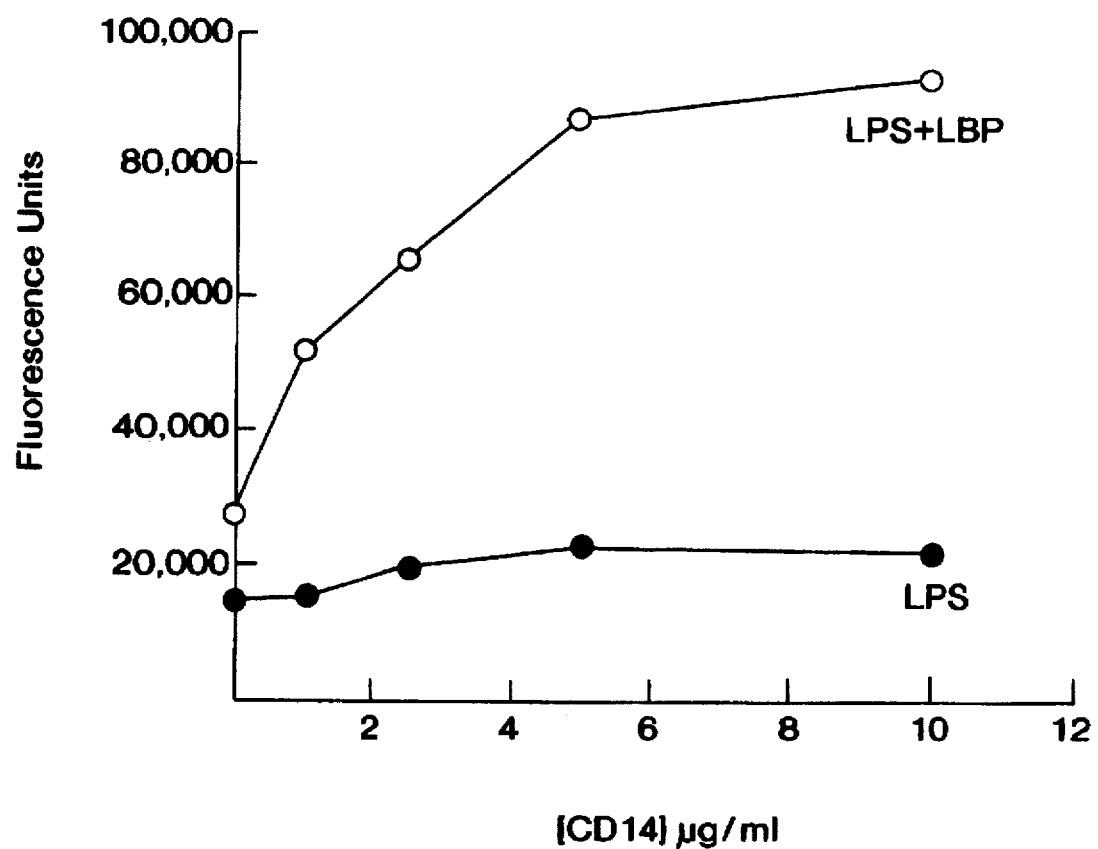
FIG. 2 illustrates the dose-response curve of the increase in FI through the LBP-mediated binding of F-LPS (LPS) to CD14 in a binding assay measured spectrophotometrically as described in Example 1. The data is plotted as described in FIG. 1. The assays were performed under two conditions: 1) LPS alone; and 2) LPS in the presence of LBP.

The results of these assays are shown in FIGS. 1 and 2 where it is seen that the addition of F-LPS to admixtures of LBP and CD14 produced an increase in FI that exhibited a CD14 concentration dependency. The maximum FI of greater than 90,000 fluorescence units plateaued at a CD14 concentration of about 10 ug/ml. In the absence of LBP, no effect was detected even after addition of 10 ug/ml of CD14 and replacement of LBP with the other LPS-binding proteins, including LPS alone (FIGS. 1 and 2), apotransferrin, lysozyme, or albumin (FIG. 1). Thus, the results of the binding assay shows that LBP is required in the assay to achieve the requisite increase in fluorescent intensity mediated through the binding to LPS to CD14.

C. Specificity of Increase in Fluorescent Intensity Determined by Specific Inhibition of Binding Assay Using Non-Fluorescent LPS To further establish the specificity of the increase in FI through the LBP-dependent binding of LPS in the binding assay of this invention described in Examples 1 and 2, varying amounts of non-fluoresceinated Re595 LPS prepared in Example 1 and ranging in concentration from 0 to 20 ug/ml were admixed to an admixture of LBP and CD14 followed by the addition of F-LPS. The concentrations of the binding assay reagents were as described in Example 2.

Figure 3:
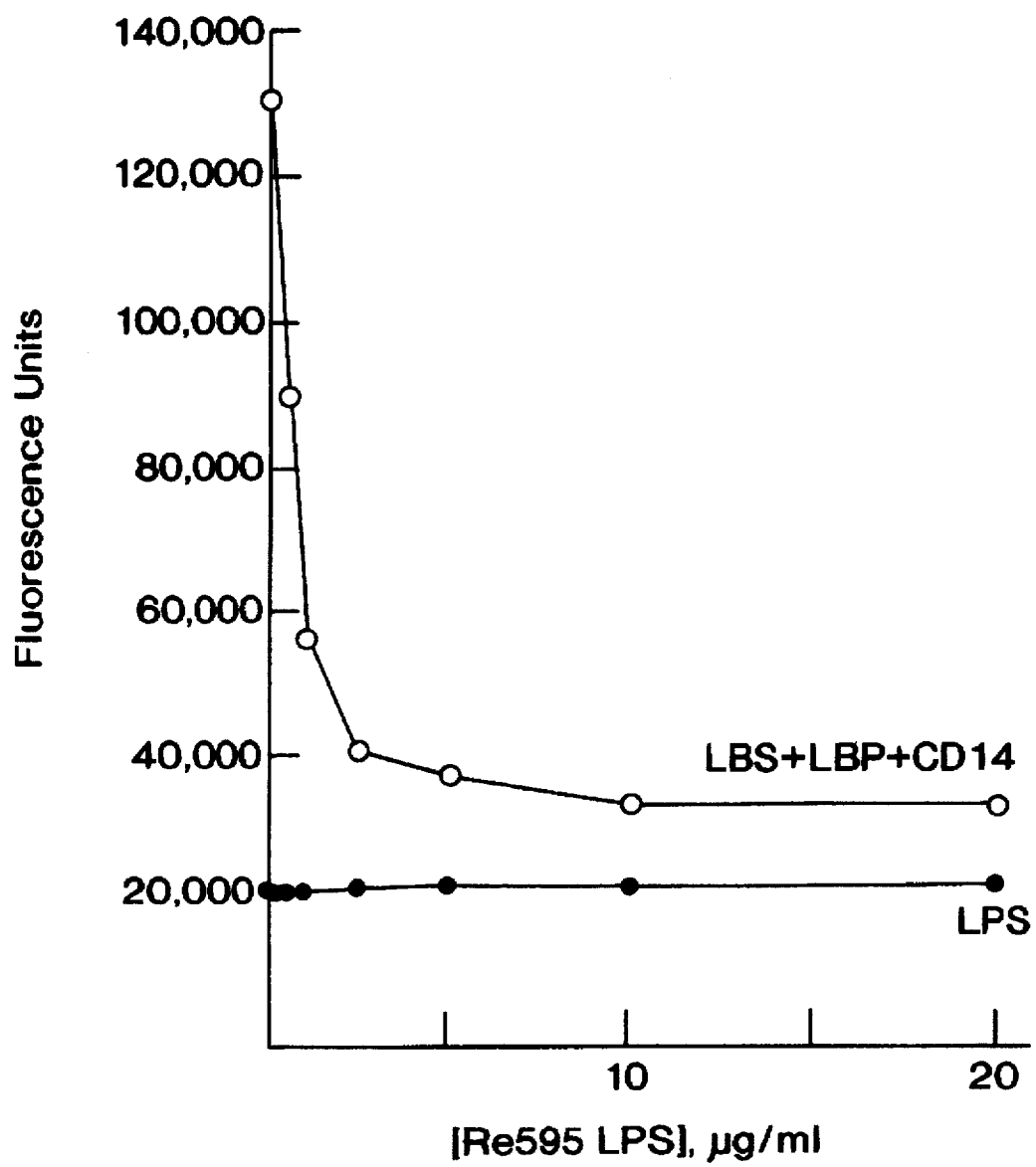
FIG. 3 illustrates the decrease in FI through the inhibition of LBP-mediated binding of F-LPS (LPS) to CD14 in the presence of unlabeled Re595 LPS ranging in concentration from 0 to 20 ug/ml. The data is plotted as described in FIG. 1. The assay was performed as described in Example 2.

As shown in FIG. 3, the non-fluoresceinated LPS efficiently competed with F-LPS by inhibiting the increase in FI with a Ki of approximately 2 ug/ml. Since quenching did not result from the addition of excess unlabeled competitor, the increase of detectable FI obtained through the binding of LPS to CD14 mediated by LBP was thus specific. In addition, other non-fluoresceinated LPS preparations such as 0111:B4 LPS, synthetic lipid A and lipid IVa demonstrated dose dependent inhibition similar to that shown in FIG. 3 with Re595 LPS. These results indicate that inhibition by added Re595 LPS is due to specific competition of lipid A-dependent binding.

3. Identification of Inhibitors of LBP-Dependent LPS Binding to CD14

A. Inhibition by Monoclonal Antibodies

Monoclonal antibodies to human CD14 or LBP have been shown to block the LBP-dependent LPS-mediated activation of CD14-bearing monocytes. See, Wright et al., *Science*, 249:1431 (1990); and Kirkland et al., *J. Biol. Chem.*, 268:24818–24823 (1993). Thus, the binding assay method of this invention can be used to determine whether inhibition of the biologic response to LPS by monoclonal antibodies to CD14 or to LBP would be reflected in an inhibition of the measured increase in fluorescence (FI) observed in admixtures of F-LPS, LBP and CD14 in the present methods.

1) Anti-CD14 Monoclonal Antibodies

Several monoclonal antibodies specific for human CD14 are evaluated for the ability to block the increase in FI after F-LPS is admixed with LBP and CD14 according to the methods described in Example 2.

Monoclonal antibodies to human CD14 were generated by somatic cell fusion between spleen cells from BALB/c mice immunized with purified human recombinant CD14 and the mouse myeloma cell line X63.Ag8.653. Several CD14-specific monoclonal antibodies (Mab) were obtained by screening against CD14 in an enzyme-linked immunoassay (EIA). Binding to native CD14 was confirmed by flow microfluorometry on CD14$^+$ cells and immunoprecipitation of biosynthetically labeled CD14. Representative anti-CD14 antibodies obtained by the above method include Mab's designated 28C5, 5G3, 4F2, 13A7, 10B7 and 26F3, and have properties as described by Kirkland et al., *J. Biol. Chem.*, 268:24818–24823 (1993).

MY-4 (IgG2a) is a commercially available anti-CD14 Mab obtained from Coulter Immunology (Hialeah, Fla.). Mab 3C10 is an anti-CD14 monoclonal antibody available from the ATCC as accession number TIB228 and described by Van Voorhis et al., *J. Exp. Med.*, 158:126–145 (1983).

The results of the present binding assays conducted using anti-CD14 antibodies indicate that selected anti-CD14 antibodies inhibit fluorescence. Control monoclonal antibodies against the unrelated proteins, prolactin or ferritin, are without effect. Thus, the assay is suitable for identifying anti-CD14 antibodies which inhibit LBP-dependent LPS-mediated cell activation.

2) Anti-LBP Monoclonal Antibodies

Several monoclonal antibodies specific for human LBP are evaluated for the ability to block the increase in FI after F-LPS is admixed with LBP and CD14 according to the methods described in Example 2.

Monoclonal antibodies to human LBP were generated by somatic cell fusion between spleen cells from BALB/c mice immunized with purified human LBP and the mouse myeloma cell line X63.Ag8.653. Several LBP-specific monoclonal antibodies (Mab) were obtained by screening against LBP in an enzyme-linked immunoassay (EIA). Bindini to LBP was confirmed by immunoprecipitation, Western Blots and competition experiments. Representative anti-LBP antibodies obtained by the above method include Mab's designated 2B5, 18G4, 1E8 and 8F5, and have properties as described by Kirkland et al., *J. Biol. Chem.*, 268:24818–24823 (1993).

A preferred anti-LBP monoclonal antibody is the Mab 28C5.

The results of the present binding assays conducted using anti-LBP antibodies indicate that selected anti-LBP antibodies inhibit fluorescence. Control monoclonal antibodies against the unrelated proteins, prolactin or ferritin, are without effect. Thus, the assay is suitable for identifying anti-LBP antibodies which inhibit LBP-dependent LPS-mediated cell activation.

The hybridoma cell lines producing Mab 28C5, Mab 1E8 and Mab 2B5 have been deposited with the American Type Culture Collection (ATCC) 12301 Parklawn Drive, Rockville, Md. 20852, U.S.A., under the provisions of the Budapest Treaty on the International Deposit of Microorganisms for the Purposes of Patent Procedure. These deposits were made on May 27, 1993, Nov. 16, 1993, and Nov. 16, 1993, and were accorded ATCC accession numbers HB 11364, HB 11490 and HB 11491, for Mabs 28C5, 1E8 and 2B5, respectively.

These deposits were made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A method for identifying a compound which inhibits lipopolysaccharide (LPS) binding to LPS binding protein (LBP), which method comprises:
   a) measuring the fluorescence emitted by a first binding reaction admixture in solution that comprises:
      i) fluoresceinated LPS, and
      ii) isolated LBP;
   b) measuring the fluorescence emitted by a second binding reaction admixture in solution that comprises:
      i) fluoresceinated LPS,
      ii) isolated LBP, and
      iii) said compound; and
   c) identifying a reduction in measured fluorescence emitted by said second binding reaction admixtures compared to said first binding reaction admixture, thereby identifying said inhibition activity of said compound.

2. The method of claim 1 wherein said fluoresceinated LPS is fluorescein-re595 LPS.

3. The method of claim 1 wherein said LBP is human or rabbit LBP.

4. The method of claim 1 wherein said fluoresceinated LPS is present in said binding reaction admixture at a concentration of from about 1 to about 100 nanograms per milliliter.

5. The method of claim 1 wherein said LBP is present in said binding reaction admixture at a concentration of from about 10 to about 1000 nanograms per milliliter.

6. A method for identifying a compound which inhibits lipopolysaccharide binding protein (LBP)-dependent binding of lipopolysaccharide (LPS) to monocyte receptor CD14, which method comprises:
   a) measuring the fluorescence emitted by a first binding reaction admixture in solution that comprises:
      i) fluoresceinated LPS,
      ii) isolated LBP, and
      iii) isolated CD14;
   b) measuring the fluorescence emitted by a second binding reaction admixture in solution that comprises:
      i) fluoresceinated LPS,
      ii) isolated LBP,
      iii) isolated CD14, and
      iv) said compound; and
   c) identifying a reduction in measured fluorescence emitted by said second binding reaction admixture compared to said first binding reaction admixture, thereby identifying said inhibition activity of said compound.

7. The method of claim 6 wherein said fluoresceinated LPS is fluorescein-re595 LPS.

8. The method of claim 6 wherein said LBP is human or rabbit LBP.

9. The method of claim 6 wherein said isolated CD14 has an amino acid residue sequence shown in SEQ ID NO 2.

10. The method of claim 6 wherein said fluoresceinated LPS is present in said binding reaction admixture at a concentration of from about 1 to about 100 nanograms per milliliter.

11. The method of claim 6 wherein said LBP is present in said binding reaction admixture at a concentration of from about 10 to about 1000 nanograms per milliliter.

12. The method of claim 6 wherein said isolated CD14 is present in said binding reaction admixture at a concentration of from about 5 to 30 micrograms per milliliter.

\* \* \* \* \*